US010016473B2

(12) United States Patent
Nwulia

(10) Patent No.: US 10,016,473 B2
(45) Date of Patent: Jul. 10, 2018

(54) METHOD, APPARATUS, AND KIT FOR THE PULSING TREATMENT OF NEURODEGENERATIVE DISEASES AND IMPAIRMENTS

(71) Applicant: Howard University, Washington, DC (US)

(72) Inventor: Evaristus A. Nwulia, Elkridge, MD (US)

(73) Assignee: Howard University DC (US)

( * ) Notice: Subject to any disclaimer, the term of this patent is extended or adjusted under 35 U.S.C. 154(b) by 455 days.

(21) Appl. No.: 14/591,780

(22) Filed: Jan. 7, 2015

(65) Prior Publication Data

US 2015/0118335 A1 Apr. 30, 2015

Related U.S. Application Data

(63) Continuation-in-part of application No. 13/793,592, filed on Mar. 11, 2013, now Pat. No. 9,101,652, which is a continuation-in-part of application No. 13/793,755, filed on Mar. 11, 2013, now Pat. No. 9,012,490.

(60) Provisional application No. 61/990,588, filed on May 8, 2014, provisional application No. 61/684,316, filed on Aug. 17, 2012, provisional application No. 61/756,892, filed on Jan. 25, 2013.

(51) Int. Cl.
| | |
|---|---|
| *A61K 36/00* | (2006.01) |
| *A61K 36/53* | (2006.01) |
| *A61K 9/00* | (2006.01) |
| *A61K 36/752* | (2006.01) |
| *A61M 16/12* | (2006.01) |
| *A61K 36/54* | (2006.01) |
| *A61M 15/00* | (2006.01) |
| *A61M 16/16* | (2006.01) |
| *A61M 16/06* | (2006.01) |
| *A61M 16/20* | (2006.01) |
| *A61M 21/00* | (2006.01) |
| *A61M 16/00* | (2006.01) |

(52) U.S. Cl.
CPC ............ *A61K 36/53* (2013.01); *A61K 9/0043* (2013.01); *A61K 36/54* (2013.01); *A61K 36/752* (2013.01); *A61M 15/0085* (2013.01); *A61M 16/12* (2013.01); *A61M 16/16* (2013.01); *A61K 9/007* (2013.01); *A61M 16/0666* (2013.01); *A61M 16/0672* (2014.02); *A61M 16/122* (2014.02); *A61M 16/162* (2013.01); *A61M 16/208* (2013.01); *A61M 21/00* (2013.01); *A61M 2016/003* (2013.01); *A61M 2021/0016* (2013.01); *A61M 2202/0208* (2013.01); *A61M 2205/8206* (2013.01); *A61M 2205/8237* (2013.01)

(58) Field of Classification Search
None
See application file for complete search history.

(56) References Cited

U.S. PATENT DOCUMENTS

| | | |
|---|---|---|
| 5,522,253 A | 6/1996 | Knight |
| 5,875,783 A | 3/1999 | Kullik |
| 6,145,503 A | 11/2000 | Smith |
| 6,506,801 B1 | 1/2003 | Yee et al. |
| 7,013,889 B2 | 3/2006 | Cronk et al. |
| 7,273,618 B2 | 9/2007 | Frey, II et al. |
| 7,703,455 B2 | 4/2010 | Bunke et al. |
| 7,740,014 B2 | 6/2010 | Djupesland |
| 7,776,312 B2 | 8/2010 | Frey, II et al. |
| 7,799,337 B2 | 9/2010 | Levin |
| 8,001,968 B2 | 8/2011 | Doty et al. |
| 8,192,718 B1 | 6/2012 | Sung et al. |
| 8,220,457 B2 | 7/2012 | Berthon-Jones et al. |
| 9,012,490 B2 | 4/2015 | Nwulia et al. |
| 9,101,652 B2 | 8/2015 | Nwulia |
| 2004/0014721 A1 | 1/2004 | Hensley et al. |
| 2005/0090520 A1 | 4/2005 | Lindquist |
| 2006/0276536 A1 | 12/2006 | Vander Jagt et al. |
| 2011/0129462 A1 | 6/2011 | Maggio |
| 2012/0053208 A1 | 3/2012 | Li et al. |
| 2012/0328701 A1 | 12/2012 | Edelson et al. |

FOREIGN PATENT DOCUMENTS

WO 2008/103346 A1 8/2008

OTHER PUBLICATIONS

Block, Controlled prospective randomised trial on the effects on pulmonary haemodynamics of the ambulatory long term use of nitric oxide and oxygen in patients with severe COPD. Thorax, (Apr. 1, 2003) vol. 58, No. 4, pp. 289-293.*
Maxwell, Patrick, and Salnikow, Konstantin, "HIF-1 An Oxygen and Metal Responsive Transcription Factor," Cancer Biology & Therapy, Jan. 2004, vol. 3, No. 1, pp. 29-35.
Mesholam, Raquelle I., et al., "Olfaction in Neurodegenerative Disease: A Meta-Analysis of Olfactory Functioning in Alzheimer's and Parkinson's Diseases," Archives of Neurology, Jan. 1998, vol. 55, No. 1, pp. 84-90.
Miwa, Naofumi, and Storm, Daniel R., "Odorant-Induced Activation of Extracellular Signal-Regulated Kinase/Mitogen-Activated Protein Kinase in the Olfactory Bulb Promotes Survival of Newly Formed Granule Cells," The Journal of Neuroscience, Jun. 1, 2005, vol. 25, No. 22, pp. 5404-5412.
Murphy, Claire, et al., "Olfactory Thresholds are Associated with Degree of Dementia in Alzheimer's Disease," Neurobiology of Aging, Jul.-Aug. 1990, vol. 11, No. 4, pp. 465-469.

(Continued)

*Primary Examiner* — Qiuwen Mi
(74) *Attorney, Agent, or Firm* — Fitch, Even, Tabin & Flannery, LLP

(57) ABSTRACT

A method, apparatus and kit have been discovered which utilize pulsed odorants, drugs, medicaments, and combinations thereof to treat diseases, symptoms of diseases and the like. In one form, the pulsed odorants, drugs, medicaments, and combinations thereof can be used to regenerate the connections of the neurons of the brain and central nervous system in the treatment of symptoms of such person afflicted with neuro-disorders, such as caused by disease or trauma.

10 Claims, 5 Drawing Sheets

(56) References Cited

OTHER PUBLICATIONS http://www.neurodegenerationresearch.eu/about/why/, 2014, Why choose Neurodegenerative diseases?

Padhye S., et al. "Perspectives on Chemopreventive and Therapeutic Potential of Curcumin Analogs in Medicinal Chemistry." Mini Reviews in Medicinal Chemistry, May 2010, vol. 10, No. 5, pp. 372-387.

PCT International Search Report and Written Opinion on Patentablility, International Patent Application PCT/US2014/013158, completed Apr. 11, 2014, 12 pages.

Perry, Elaine, et al., "Medicinal Plants and Dementia Therapy: Herbal Hopes for Brain Aging?" CNS Neuroscience & Therapeutics, 2011, vol. 17, pp. 683-698.

Pfeiffer, Erika, et al., "Studies on the Stability of Turmeric Constituents." Journal of Food Engineering, 2003, vol. 56, pp. 257-259.

Rochefort, Christelle, et al., Enriched Odor Exposure Increases the Number of Newborn Neurons in the Adult Olfactory Bulb and Improves Odor Memory, The Journal of Neuroscience, vol. 22, No. 7, Apr. 1, 2002, pp. 2679-2689.

Ross, T. M., et al., "Intranasal administration of interferon beta bypasses the blood-brain barrier to target the central nervous system and cervical lymph nodes: a non-invasive treatment strategy for multiple sclerosis," Journal of Neuroimmunology, 2004, vol. 151, pp. 66-77.

Ruan, Yang, et al., "Olfactory Dysfunctions in Neurodegenerative Disorders," Journal of Neuroscience Research, Sep. 2012, vol. 90, No. 9, pp. 1693-1700.

Saiyudthong, Somrudee, and Marsden, Charles A., "Acute Effects of Bergamot Oil on Anxiety-Related Behavious and Corticosterone Level in Rats," Phytotherapy Research, 2011, vol. 25, pp. 858-862.

Scharfman, Helen E., and Chao, Moses V., "The Entorhinal Cortex and Neurotrophin Signaling in Alzheimer's Disease and Other Disorders," Cognitive Neuroscience, Sep.-Dec. 2013, vol. 4 Nos. 3-4, pp. 123-135.

Schulz, Carla, et al., Central Nervous and Metabolic Effects of Intranasally Applied Leptin, Endocrinology, vol. 145, No. 6, Jun. 2004, pp. 2696-2701.

Shapiro, Lee A., et al., "Olfactory enrichment enhances the survival of newly born cortical neurons in adult mice," NeuroReport, Jul. 2, 2007, vol. 18, No. 10, pp. 981-985.

Shishodia, Shishir, et al., "Modulation of Transcription Factors by Curcumin," The Molecular Targets and Therapeutic Uses of Curcumin in Health and Disease, Editors: Bharat B. Aggarawal et al., Advances in Experimental Medicine and Biology, 2007, vol. 595, pp. 127-148.

Simmons, Peter A., and Getchell, Thomas V., "Physiological Activity of Newly Differentiated Olfactory Receptor Neurons Correlated With Morphological Recovery From Olfactory Nerve Section in the Salamander," Journal of Neurophysiology, Mar. 1981, vol. 45, No. 3, pp. 529-549.

Snodgrass, Kat, "Alzheimer's protein kills nerve cells in nose, [online]." Retrieved from the Internet on Jul. 11, 2012: <URL: http://www.eurekalert.org/pub_releases/2011-09/sfn-apk092611.php>, Sep. 27, 2011, 1 page.

Sui, Zhihua, et al., "Inhibition of the HIV-1 and HIV-2 Proteases by Curcumin and Curcumin Boron Complexes," Bioorganic & Medicinal Chemistry, 1993, vol. 1, No. 6, pp. 415-422.

Taher, Mohiuddin M., et al., "Curcumin inhibits ultraviolet light induced human immunodeficiency virus gene expression," Molecular and Cellular Biochemistry, 2003, vol. 254, pp. 289-297.

Wang, Ying-Jan, et al., "Stability of Curcumin in Buffer Solutions and Characterization of its Degradation Products," Journal of Pharmaceutical and Biomedical Analysis, 1997, vol. 15, pp. 1867-1876.

Weinberg, Eugene D., and Miklossy, Judith, "Iron Withholding: A Defense Against Disease," Journal of Alzheimer's Disease, 2008, vol. 13, pp. 451-463.

White, Brett, et al., "Does turmeric relieve inflammatory conditions?" The Journal of Family Practice, Mar. 2011, vol. 60, No. 3, pp. 155-166.

Wilson, Robert S., et al., "Odor Identification and Mortality in Old Age," Chemical Senses, Jan. 2011, vol. 36, No. 1, pp. 63-67.

Woo, Cynthia C., et al., "Exposure to a broad range of odorants decreases cell mortality in the olfactory bulb," NeuroReport, May 29, 2006, vol. 17, No. 8, pp. 817-821.

Xu, Ying, et al., "Curcumin reverses impaired hippocampal neurogenesis and increases serotonin receptor 1A mRNA and brain-derived neurotrophic factor expression in chronically stressed rats," Brain Research, 2007, vol. 1162, pp. 9-18.

Yadav, Babasaheb D., "Study of New Curcumin Analogs for the Treatment of ER-alpha Negative Breast Cancers," Doctoral Thesis, The University of Otago, Dunedin, New Zealand, Jan. 4, 2012, 6 pages.

Youngentob, Steven L., et al., "Odorant Threshold Following Methyl Bromide-Induced Lesions of the Olfactory Epithelium," Physiology & Behavior, 1997, vol. 62, No. 6, pp. 1241-1252.

Zhang, Laura, et al., "Curcuminoids enhance amyloid-beta uptake by macrophages of Alzheimer's disease patients," Journal of Alzheimer's Disease, 2006, vol. 10, pp. 1-7.

Letters to the Editors, "Suicidal Ideation Associated With Duloxetine Use: A Case Series," Journal of Clinical Psychopharmacology, Feb. 2008, vol. 28, No. 1, pp. 101-122.

Du, Zhi-Yun, et al., "Curcumin Analogs as Potent Aldose Reductase Inhibitors," Archiv der Pharmazie Chemistry in Life Science, 2006, vol. 339, pp. 123-128.

Nema, Sandeep, et al., "Excipients and Their Use in Injectable Products," Review Article, PDA Journal of Pharmaceutical Science & Technology, Jul.-Aug. 1997, vol. 51, No. 4, pp. 166-171.

Ribeiro, Sofia, and Horuk, Richard, "The clinical potential of chemokine receptor antagonists," Pharmacology & Therapeutics, 2005, vol. 107, pp. 44-58.

Albers, Mark W., et al., "At the Interface of Sensory and Motor Dysfunctions and Alzheimer's Disease," Alzheimer's & Dementia, Jan. 2015, 11(1), pp. 70-98.

Alvarez, Susana, et al., "Human immunodeficiency virus type 1 envelope glycoprotein 120 induces cyclooxygenase-2 expression in neuroblastoma cells through a nuclear factor-κ b and activating protein-1 mediated mechanism," Journal of Neurochemistry, 2005, vol. 94, pp. 850-861.

Anand, Preetha, et al., "Bioavailability of Curcumin: Problems and Promises," Molecular Pharmaceutics, Nov. 14, 2007, vol. 4, No. 6, pp. 807-818.

Ataie, Amin, et al., "Curcumin Exerts Neuroprotective Effects Against Homocysteine Intracerebroventricular Injection-Induced Cognitive Impairment and Oxidative Stress in Rat Brain," Journal of Medicinal Food, 2010, vol. 13, No. 4, pp. 821-826.

Atsumi, Toshiko, and Tonosaki, Keiichi, "Smelling lavender and rosemary increases free radical scavenging activity and decreases cortisol level in saliva," Psychiatry Research, vol. 150, 2007, pp. 89-96.

Bagetta, Giacinto, et al., "Neuropharmacology of the essential oil of bergamot," Fitoterapia, vol. 81, 2010, pp. 453-461.

Bai, Xue-Feng, et al., "Nasal administration of myelin basic protein prevents relapsing experimental autoimmune encephalomyelitis in DA rats by activating regulatory cells expressing IL-4 and TGF-β mRNA," Journal of Neuroimmunology, vol. 80, 1997, pp. 65-75.

Barthelemy, S., et al., "Curcumin and curcumin derivatives inhibit Tat-mediated transactivation of type 1 human immunodeficiency virus long terminal repeat," Research in Virology, 1998, vol. 149, pp. 43-52.

Baum, Larry, et al., "Curcumin interaction with copper and iron suggests one possible mechanism of action in Alzheimer's disease animal models," Journal of Alzheimer's Disease, 2004, vol. 6, pp. 367-377.

Benedict, Christian, et al., "Intranasal insulin improves memory in humans," Psychoneuroendocrinology, vol. 29, 2004, pp. 1326-1334.

Born, Jan, et al., "Sniffing neuropeptides: a transnasal approach to the human brain," Nature Neuroscience, vol. 5, No. 6, Jun. 2002, pp. 514-516.

Bovetti, Serena, et al., "Olfactory Enrichment Influences Adult Neurogenesis Modulating GAD67 and Plasticity-Related Molecules Expression in Newborn Cells of the Olfactory Bulb," PLoS One, vol. 4, Issue 7, Jul. 2009, 10 pages.

(56) References Cited

OTHER PUBLICATIONS

Ceccarelli, Ilaria, et al., "Effects of long-term exposure of lemon essential oil odor on behavioral, hormonal and neuronal parameters in male and female rats," Brain Research, vol. 1001, 2004, pp. 78-86.
Chen, Xue-Qing, et al., "Delivery of Nerve Growth Factor to the Brain via the Olfactory Pathway," Journal of Alzheimer's Disease, vol. 1, 1998, pp. 35-44.
Chiu, Simon S., et al., "Differential Distribution of Intravenous Curcumin Formulations in the Rat Brain," Anticancer Research, 2011, vol. 31, pp. 907-911.
Cole, Greg M., et al., "Neuroprotective Effects of Curcumin," Advances in Experimental Medicine and Biology, 2007, vol. 595, pp. 197-212.
Comford, Eain M., and Comford, Marcia E., "New systems for delivery of drugs to the brain in neurological disease," The Lancet Neurology, vol. 1, Sep. 2002, pp. 306-315.
Conteas, Chris N., et al., "Treatment of HIV-Associated Diarrhea with Curcumin," Digestive Diseases and Sciences, 2009, vol. 54, pp. 2188-2191.
Cos, Paul, et al., "Plant-Derived Leading Compounds for Chemotherapy of Human Immunodefiency Virus (HIV) Infection—An Update (1998-2007)," Planta Medica, 2008, vol. 74, pp. 1323-1337.
Costanzo, Richard M., "Neural Regeneration and Functional Reconnection Following Olfactory Nerve Transection in Hamster," Brain Research, vol. 361, 1985, pp. 258-266.
Devanand, D. P., et al., "Olfactory Deficits in Patients with Mild Cognitive Impairment Predict Alzheimer's Disease at Follow-up," The American Journal of Psychiatry, Sep. 2000, vol. 157, No. 9, pp. 1399-1405.
Doty, Richard L., et al., "Presence of Both Odor Identification and Detection Deficits in Alzheimer's Disease," Brain Research Bulletin, May 1987, vol. 18, No. 5, pp. 597-600.
Du, Zhi-yun, et al., "Alpha-Glucosidase inhibition of natural curcuminoids and curcumin analogs," European Journal of Medicinal Chemistry, 2006, vol. 41, pp. 213-218.
Etchamendy, Nicole, et al., "Alleviation of a Selective Age-Related Relational Memory Deficit in Mice by Pharmacologically Induced Normalization of Brain Retinoid Signaling," The Journal of Neuroscience, Aug. 15, 2001, vol. 21, No. 16, pp. 6423-6429.
Faturi, Claudia Brito, et al., "Anxiolytic-like effect of sweet orange aroma in Wistar rats," Progress in Neuro-Psychopharmacology & Biological Psychiatry, vol. 34, 2010, pp. 605-609.
Fuchs, James R., et al., "Structure-activity relationship studies of curcumin analogues," Bioorganic & Medicinal Chemistry Letters, 2009, vol. 19, pp. 2065-2069.
Gheusi, Gilles, et al., "Importance of newly generated neurons in the adult olfactory bulb for odor discrimination," Proceedings of the National Academy of Sciences, vol. 97, No. 4, Feb. 15, 2000, pp. 1823-1828.
Gilden, Dave, and Smart, Theo, "Curcumin Trial Finds No Activity," GMHC Treatment Issues, Feb. 1996.
Gomez-Pinilla, Fernando, et al., "Natural mood foods: The actions of polyphenols against psychiatric and cognitive disorders," Nutritional Neuroscience, May 2012, vol. 15, No. 3, pp. 127-133.
Gopinath, Bamini, et al., "The Association Between Olfactory Impairment and Total Mortality in Older Adults," The Journals of Gerontology, Series A, Biological Sciences and Medical Sciences, Feb. 2012, vol. 67, No. 2, pp. 204-209.
Gordon, Odaine N., et al., "Vanillin and ferulic acid: not the major degradation products of curcumin," Cell Press, Trends in Molecular Medicine, Jul. 2012, vol. 18, No. 7, pp. 361-363.
Gozes, Illana, "Neuroprotective peptide drug delivery and development: potential new therapeutics," Trends in Neurosciences, Dec. 2001, vol. 24, No. 12, pp. 700-705.
Graziadei, Pasquale P. C., et al., "Regeneration of olfactory axons and synapse formation in the forebrain after bulbectomy in neonatal mice," Proceedings of the National Academy of Sciences of the United States of America, Oct. 1978, vol. 75, No. 10, pp. 5230-5234.
Graziadei, P. P. C., and Graziadei, G. A. Monti, "Neurogenesis in neuron regeneration in the olfactory system of mammals. I. Morphological aspects of differentiation and structural organization of the olfactory sensory neurons," Journal of Neurocytology, 1979, vol. 8, pp. 1-18.
Gupta, S. P., et al., "Design and Development of Integrase Inhibitors as Anti-HIV Agents," Current Medicinal Chemistry, 2003, vol. 10, pp. 1779-1794.
Harding, Joseph W., et al., "Denervation of the Primary Olfactory Pathway in Mice. V. Long-term Effect of Intranasal ZnSO4 Irrigation on Behavior, Biochemistry and Morphology," Brain Research, 1978, vol. 140, pp. 271-285.
Hsu, Chih-Hung, and Cheng, Ann-Lii, "Clinical Studies With Curcumin," Advances in Experimental Medicine and Biology, 2007, vol. 595, pp. 471-480.
Hurley, Laura L., et al., "Antidepressant-like effects of curcumin in WKY rat model of depression is associated with an increase in hippocampal BDNF," Behavioural Brain Research, 2012, pp. 1-4.
James, John S., "Curcumin: Clinical Trial Finds No Antiviral Effect," The Body, AIDS Treatment News, Mar. 1, 1996, No. 242, 3 pages.
Komiya, Migiwa, et al., "Lemon oil vapor causes an anti-stress effect via modulating the 5-HT and DA activities in mice," Behavioural Brain Research, 2006, vol. 172, pp. 240-249.
Kulkami, S. K., et al., "Potentials of Curcumin as an Antidepressant," The Scientific World Journal, 2009, vol. 9, pp. 1233-1241.
Kulkami, S. K., et al., "Evaluation of Antidepressant-Like Activity of Novel Water-Soluble Curcumin Formulations and St. John's Wort in Behavioral Paradigms of Despair," Pharmacology, 2012, vol. 89, pp. 83-90.
Kumar, Anil, et al., "Effect of Curcumin on Intracerebroventricular Colchicine-Induced Cognitive Impairment and Oxidative Stress in Rats," Journal of Medicinal Food, 2007, vol. 10, No. 3, pp. 486-494.
Liao, Kai, et al., "Enriched odor exposure decrease tau phosphorylation in the rat hippocampus and cortex," Neuroscience Letters, 2012, vol. 507, pp. 22-26.
Liu, J. P., et al., "Herbal medicines for treating HIV infection and AIDS (Review)," The Cochrane Library, 2009, Issue 1, 30 pages.
Liu, Yuanbin, et al., "A broadly neuroprotective derivative of curcumin," Journal of Neurochemistry, 2008, vol. 105, pp. 1336-1345.
Mandairon, Nathalie, et al., "Broad activation of the olfactory bulb produces long-lasting changes in odor perception," Proceedings of the National Academy of Sciences of the United States of America, Sep. 5, 2006, vol. 103, No. 36, pp. 13543-13548.
Manna, Sunil K., et al., "Oleandrin Suppresses Activation of Nuclear Transcription Factor-κb, Activator Protein-1, and c-Jun NH2-Terminal Kinase," Cancer Research, Jul. 15, 2000, vol. 60, pp. 3838-3847.
Martončíková, Marcela, et al., "Odor enrichment influences neurogenesis in the rostral migratory stream of young rats," Acta Histochemica, 2011, vol. 113, pp. 326-332.
Masoumi, Ava, et al., "1-alpha,25-dihydroxyvitamin D3 Interacts with Curcuminoids to Stimulate Amyloid-beta Clearance by Macrophages of Alzheimer's Disease Patients," Journal of Alzheimer's Disease, 2009, vol. 17, pp. S1-S4.

* cited by examiner

METHOD, APPARATUS, AND KIT FOR THE PULSING TREATMENT OF NEURODEGENERATIVE DISEASES AND IMPAIRMENTS

CROSS-REFERENCE To RELATED APPLICATIONS

This application claims benefit of U.S. Provisional Application No. 61/990,588, filed May 8, 2014, and is also a continuation-in-part of U.S. application Ser. No. 13/793,592, filed Mar. 11, 2013, which claims benefit of U.S. Provisional Application No. 61/684,316, filed Aug. 17, 2012, and to application Ser. No. 13/793,755, filed Mar. 11, 2013, which claims benefit of U.S. Provisional Application No. 61/756,892, filed Jan. 25, 2013 and U.S. Provisional Application No. 61/684,316, filed Aug. 17, 2012, the disclosures of which are hereby incorporated herein by reference in their entirety.

FIELD

This application relates to the use of odorants, drugs, and/or medicaments for treating various conditions and, more particularly, pulsing odorants, drugs, and/or medicaments to treat various conditions, along with an apparatus and kit for carrying out the method.

BACKGROUND

Alzheimer's disease and dementia are diseases which result in a progressive deterioration of neurons in the brain. This causes cognitive deterioration and changes in behavior. With dementia and Alzheimer's disease, there is loss of short-term memory and minor forgetfulness which becomes greater as the illness progresses to major memory loss with a relative preservation of older memories. As the disease progresses even further, there is cognitive or intellectual impairment which extends to language degeneration (having difficulty remembering words to being completely unable to speak, read, or write), loss of the ability to execute or carry out learned purposeful movements, and a loss of ability to recognize objects, persons, sounds, shapes, or smells.

Neurons are cells which transmit information via synapses. Neurons connect to each other to form neural networks. Neurons are electrically excitable cells which transmit information by electrical and chemical signaling by synapses which establish connections with other neuron cells. With the progression of dementia, Alzheimer's disease, and other neurodegenerative diseases, the connectivity of the neurons are adversely affected, such as by the generation of plaque and abnormal proteins called tau proteins.

Human olfaction declines with advancing age, with rates of anosmia (loss of sense of smell) approaching 50% of populations 65 and 80 years old, and approximately 75% in those over 80 years. Such diminution in olfaction influences enjoyment of food, nutrition, physical and emotional well-being, quality of life, and safety from fire hazard or from ingestion of contaminated food. Indeed, numerous epidemiologic studies in aging populations now show that olfactory loss predicts dementia, Alzheimer's disease and excess mortality. Therefore, any scientific advances that delay, prevent or reverse age-related olfactory dysfunction, including sense of smell, would have a profound impact at every aspect of our society given the present demographic shift with an exponentially increasing proportion of elderly persons and the growing percentage of those affected by cognitive decline.

The olfactory system (the system which permits humans to sense odors) is one of the most neuroplastic systems in the adult mammal. In the periphery, neurons are continuously generated in the olfactory neuroepithelium and replace older olfactory receptor neurons. These neurons project to the olfactory bulb, another area where neurons are continuously added throughout the life. The primary outputs of the olfactory bulb are to the primary olfactory cortex (POC), which consists of the anterior olfactory nucleus, olfactory tubercle, piriform cortex, periamygdaloid cortex, entorhinal cortex, central amygdaloid nuclei, and nucleus of the lateral olfactory tract. Evidence from neurobiological studies reveals that degenerative changes in these regions underlie age-associated olfactory and cognitive loss. Interestingly, these olfactory regions possess remarkable capacity for activity-dependent neuroplasticity (changes in neural pathways and synapses) in adult mammals.

However, primary neuronal pathways to olfactory regions of the brain generally desensitize within a short period of time. For example, primary neural pathways may desensitize in about one minute. Further, secondary pathways also desensitize within a short period of time, such as in 2-3 minutes. Other pathways may desensitize in shorter or longer periods of time such that the odorants become less efficacious over periods of time. This is especially the case for the intranasal delivery of odorants for the treatment of neurodegenerative diseases where the odorants positively affect olfactory regions of the brain.

Moreover, intranasal administration with positive pressure compared to just breathing room air provides a significant increase in uptake of the odorants and the surprising effect that the odorants have on reversal of symptoms of dementia, Alzheimer's disease and other diseases and traumas. In one form, the inside of human nose is enriched as the odorants exit the cannula and contact olfactory tissue in a positive pressure system as compared to simply breathing room air.

SUMMARY

Translating these basic science findings into human benefits for treatment and prevention of age-associated olfactory loss would require highly innovative approaches to efficiently engage the primary olfactory pathway. Primarily this is due to the challenge posed by the rapid (within few seconds) desensitization of the olfactory sensory neuron (OSN), olfactory bulb and primary olfactory cortex (POC) to continuous stimulations by odorants. While investigating the time course of neural response underlying desensitization to odorant stimulation, it has been observed that short short-duration stimulus, such as less than about 10 seconds, consistently activated regions in the POC. But following moderate- and long-duration stimulus, such as greater than about 15 seconds, the POC (piriform, entorhinal cortex, amygdala) and the hippocampus show a short, phasic increase in the signal, followed by a prolonged decrease below baseline.

The intervals between repetitive deliveries of olfactory stimulants also matters significantly, as short intervals of repeated stimulation leads to sensory adaptation peripherally. Other important challenges to implementation of olfactory enrichment treatment in humans include: paucity of information on the best odoriferous molecules to effectively engage the diverse populations of odorant receptors (OR)

peripherally; questionable reliability in the consistency of the composition of odorants used for olfactory stimulation; and questionable reliability in the dosage amount of odorants delivered during each olfactory chemosensory stimulation treatment. None of the animal studies provide solution to these challenges. An olfactory chemosensory stimulation device, known as the Olfactory Treatment Delivery System (OTDS), has been developed for continuous chemosensory stimulation. However, olfactory activation in the POC is compromised by rapid desensitization. Therefore, shorter duration delivery, pulsed delivery and other combinations of delivery of odorants, drugs, and the like are provided herein to surprisingly and significantly increase the effectiveness of odorants, drugs, medications and combinations thereof to stimulate and reconstitute neurons in selected areas of the brain.

The olfactory system beginning in the nose and ending in the cortex and central structures of the brain is the only currently known part of the adult mammalian brain capable of stimulation and regeneration. A method, apparatus and kit have been discovered which stimulate and regenerate the connections of the neurons of the brain and central nervous systems such that connectivity of the neurons is improved to effect improvement in memory loss, language degeneration, loss of the ability to execute or carry out learned purposeful movements, and a loss of ability to recognize objects, persons, sounds, shapes, or smells. These may also be suitable for treating other diseases and/or symptoms of diseases, conditions, and/or syndromes. For example, the method, kit, and/or apparatus may be suitable for treating symptoms of PTSD, autism and other diseases, conditions and/or syndromes.

The method includes the delivery of one odorant and/or a blend of olfactory enrichment odorants, drugs, medicaments, and combinations thereof to and through the nose with the delivery of the odorants being under a positive pressure to effect air flow with the odorant at a room temperature (25 degrees C.) delivery rate of air containing odorant of from about 0.5 to about 2 liters per minute.

Stimulation of the olfactory neurons in the nose by the odorant blend stimulate neurogeneis (new brain development) in the olfactory brain regions affected neuro-impairments caused by disease or trauma including a cognitive impairment which is a prodromal state in the development of dementia, traumatic brain injury affecting the olfactory regions of the brain. These regions include the frontal lobe, post stroke brain damage involving the frontal lobe regions and olfactory cortices of the brain, Parkinson's disease, schizophrenia, chronic depression, post-traumatic stress disorders. The stimulation of neurogeneis effects a reversal of brain impairments caused by the latter diseases and injuries. In a very important aspect, stimulation of the olfactory neurons in the nose by the odorant blends described herein stimulate neurogeneis in the olfactory brain regions affected by Alzheimer's and other types of dementia and reverse neuropathologies of Alzheimer's disease and dementia, namely hyperphoshorylation of neurofibrillary tangles and tau proteins.

In one form, the blend of odorants includes a blend of a plurality of odors including at least two of the group consisting of *citrus* (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise at a positive pressure to affect air flow with the odorant delivery rate of from about 0.5 to about 2 liters per minute. In another aspect, at least three of the odors should be used.

In one aspect, the odorants include a blend of *citrus* (orange), lemon, rosemary and cinnamon at a positive pressure to affect air flow with the odorant delivery rate of from about 0.5 to about 2 liters per minute. The odorants are dispersed in a media which permits them to be swept into the nose for intranasal application of the odorants. In an important aspect, the media is a pharmaceutically acceptable oil, such as mineral oil.

Further, the odorant can be delivered for a relatively short period of time and/or are pulsed such that a treatment regimen includes a period of delivery of the odorant, followed by a rest period, followed by another period of delivery of the odorant. In one form, the odorant can be delivered for less than about 10 seconds before a rest period begins. In another form, the odorant can be delivered for less than about 45 seconds before a rest period begins. In one form, the odorant can be delivered for less than about 10 minutes before a rest period begins. In one form, the rest period(s) may range from about 1 second to about 600 seconds between pulses. Further, it should be appreciated that the odorant may be replaced with and/or used in combination with a blend of odorants, one or more drugs, one or more medicaments, and the like.

The odorants are in a concentration for each odorant in the range of from about 1 to about 6 weight percent and are driven through the nose to contact olfactory tissue and olfactory receptor neurons. The method brings odorants in contact to this tissue in constant flow or pressure, which is needed to stimulate regeneration (or birth) of olfactory sensory system, which in turn, stimulates the olfactory bulb and olfactory cortices to be active by the intranasal administration of a blend of odorants dispersed in a media, the odorant blends include at least two, preferably three, of the odorants *citrus* (orange), lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise by pumping the blend as part of a flow of gas which includes oxygen and odorant blend. The flow created by a pump creates a positive pressure to create a flow of oxygen and odorant blend through the nose. The concentration of the blend, the ratio of odorants, the rate of flow of the blend and oxygen, a time of treatment, and the ratios of odorants in the blend effective for effecting an improved neuro-function of a person afflicted with the neurodegenerative disease or trauma. In an important aspect for a subject afflicted with a neurodegenerative disease (such as Alzheimer's disease and/or dementia), the concentration of the odorant blend, the ratio of odorants, the rate of flow of the blend and oxygen, a time of treatment, and the ratios of odorants in the blend effective for providing an improvement of at least 50%, preferably 100% and even more preferably 150% in short-term verbal memory of a person afflicted with the neurodegenerative disease, the improvement being measured by a California Verbal Learning Test, Adult, Version 2.

The time of treatment can vary depending on the length of pulses, number of pulses, parts of the body being treated, odorants, drugs, medicaments, and the like. In one form, each treatment of pulses can be from about 1 minute to about 1 hour per day. The method contemplates a treatment with a concentration of odorants at positive pressures for a time which effects new brain development (i.e. neuroplasticity) and reversal of pathological features of Alzheimer's disease or dementia in mammals.

According to one form, a method for activating selected areas of a user's brain with active ingredients is provided. The method includes delivering at least one active ingredient by pulsing by positive pressure a flow of the at least one active ingredient dispersed in a gas and controlling the area of the brain being activated by selecting a pulse and rest period that will selectively stimulate the selected area of the brain.

The apparatus used to deliver the odorants includes a pump, an air filter, a flow meter, a check valve, an odorant chamber and a cannula configured to deliver the odorant to users afflicted with the neuro degeneration disease. The odorant chamber contains the blend of odorants which are pleasant, tolerable and effect enrichment to human memory after or during the deleterious effects of Alzheimer's disease and dementia and other neurodegenerative diseases. The pump generates a current of filtered air directed into the odorant chamber through a tube with flow-directed valves. This flow is channeled through a user-controlled flow meter, on the outside of the device, for regulation of the rate of flow of odorant containing air/oxygen to the nose. The cannula directing the flow to the nose comes in different shapes and sizes, depending on the shape of a user's nose. The inside of human nose is enriched as the odorants exit the cannula and contact olfactory tissue.

In another aspect, a kit is provided where the kit which includes an apparatus which is configured for the administration of the odorant, drug, medicament, and/or combination thereof. The apparatus in the kit comprises a pump; a line which is effective for supplying air to a vessel configured to contain a blend of odorants; a line from the vessel to a cannula configured for lodgment into the nose, the pump being configured to provide a positive pressure and a flow of gas into the cannula and nose at a rate of from about 0.5 to about 2 liters per minute; and at least one additional vessel which includes a second vessel containing at least one odorant, drug, medicament, or combination thereof. The kit is configured for administering the odorant, drug, medicament, and/or combination thereof including pumping the odorant as a part of a flow of gas which includes oxygen and odorant. The flow created by the pump creates a positive pressure to create a flow of oxygen and odorant through the nose. The concentration of the odorant, the ratio of odorant/drug/medicament, the rate of flow of the odorant and oxygen, and a time of treatment are effective for providing an improvement of at least 50%, preferably 100% and even more preferably 150% in short-term verbal memory of a person afflicted with the neurodegenerative disease, the improvement being measured by a California Verbal Learning Test, Adult, Version 2. The kit also may include instructions as to the time of administration of the blend, such as daily use for one month.

DETAILED DESCRIPTION

Figure 1:
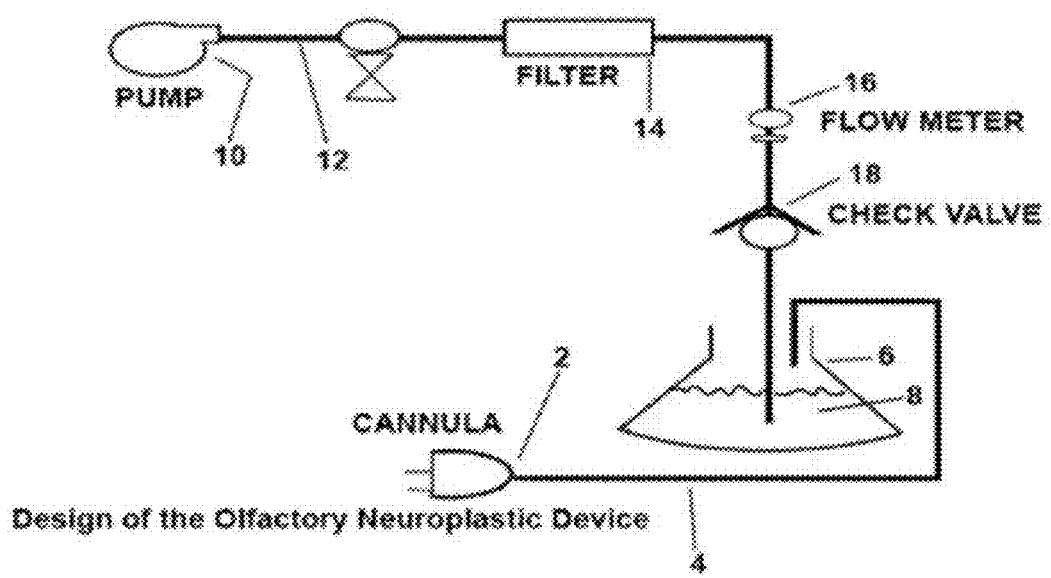
FIG. 1 is an illustration of one form of a device for administration of at least one active ingredient.

In one form, a repetitive Olfactory Chemosensory Stimulation (rOCS) paradigm, and development of an OTDS device are provided herein. It has been unexpectedly discovered that by pulsing air and/or oxygen coupled with at least one active ingredient, such as an odorant, drug, medicament, or combination thereof, much of the desensitization that occurs from prolonged exposure to the materials can be minimized or otherwise avoided. In other words, overall treatment periods of the at least one odorant, drug, medicament, or combination can be shortened using a pulsed approach than if the same material were continuously delivered.

It should be appreciated that when the term odorant is used, blends of odorants may also be used in a similar manner unless specifically stated otherwise. Further, other materials such as drugs, medicaments, and the like, may be used in the place of the odorant and/or in combination with the odorant as described herein. For example, curcumin and/or curcumin analog may be used in place of and/or in combination with one or more odorants. Similarly, other drugs, medicaments and other materials may be used.

In one form, an active ingredient, such as at least one odorant, drug, medicament, or combination thereof, may be administered to a user in a pulsed manner whereby a plurality of active delivery periods and rest periods are used. For example, each active delivery period can include delivery of at least one active ingredient followed by a rest period whereby no active ingredient is delivered to the user. A plurality of the active delivery and rest periods can be combined for a treatment regimen.

A variety of different active ingredients may be used. For example, a plurality of different odorants may be used. Such odorants may include *Rosmarinus officinalis* (Rosemary), *Citrus sinensis* (Orange), *Citrus bergamia* (Bergamot orange), *Citrus limon* (Lemon), *Lavendular augustifolia* (Lavender), and *Cinnamon Zeylanicum* (Cinnamon) which are classified as Part 182 (Substances Generally Recognized as Safe) under FDA CFR—Code of Federal Regulations Title 21. The compounds are components of human food and have been detected in human blood following ingestion. By diluting each of these odorants in polyethylene glycol (PEG) 400 (Sigma) serially, it was determined the threshold concentration (v/v) perceivable by all 20 individuals (age range 20-65) during 2-seconds olfactory threshold tasks. The maximum threshold of detection by all subjects was 2% (for Rosemary). The minimum tolerable concentration by volunteers was 6% (for cinnamon).

In one aspect, the blend of odorants includes sweet orange also called *citrus Sinensis*. Bergamont orange also called *citrus bergamia* also can be used in lieu of sweet orange or blended with sweet orange. The blend further includes lemon oil also called *citrus limon*. As used herein, "*citrus*," as opposed to "*citrus limon*" means sweet orange or bergamont orange. The odorant blend also includes Cinnamon oil also known as *cinnamomum zeylanicum* and rosemary oil also called *rosmarinus officinalis*. Odorants which are not from a botanical source such as *cinnamonum zeylanicum*, but are flavorings which mimic the botanical sourced odorant also may be used.

Other active ingredients may also be used such as drugs, medicaments, and the like. Further, the active ingredients may be used individually, in combination with one another and in combination with other types of active ingredients. For example, blends of odorants, blends of drugs, blends of medicaments, blends of odorants with drugs, and the like may be used. In one form, curcumin may be used.

Additionally, the active ingredients may be further processed to increase the concentration of one or more components therein. For example, rosemary may be used, but may be processed such that the rosemary contains a higher concentration of carnosic acid than naturally occurs. For example, the concentration of carnosic acid may be increase to be at least about 3 wt. %. In other forms, the carnosic acid concentration is increased to at least about 10 wt. %. The increased carnosic acid may increase the efficacy of other active ingredients administered to the user.

In one form, the duration of each active delivery period and/or rest period may be provided to achieve stimulation of different portions of a user. The active delivery period may be from about 1 to about 600 seconds per period before a rest period. For example, in one form, the active delivery period is about 1 to about 10 seconds to stimulate a first portion of the user. In one form, the active delivery period is about 30 to about 45 seconds to stimulate a second portion of the user. In one form, the active delivery period is about 60 to about 120 seconds to stimulate a third portion of the user.

Further, in addition to pulsing active delivery and rest periods, the active ingredients delivered may also change from one active delivery period to the next. In this regard, the user's olfactory system may be "confused" as to what the next active ingredient may be. This may enhance the efficacy through the "confusion."

In one form, a device is provided for olfactory activation. The device consists of a pump, filter, flow meter, check valve, odorant chambers, and cannula. The pump generates a current of filtered air directed into the odorant chamber through a tube with flow-directed valves. This flow is channeled through a user-controlled flow meter, on the outside of the device, for regulation of the rate of flow of odorant containing air/oxygen to the nose. The pump is operated with DC current supplied by a rechargeable battery. The apparatus has a housing to accommodate the battery and an outlet to effect recharging.

For example, referring to FIG. 1, the apparatus includes cannula 2 having a conduit 4 into an odorant chamber 6 containing a blend of odorants 8. Pump 10 pumps air at a positive pressure through conduit 12 to filter 14 and flow meter 16 past check valve 18 into the odorant chamber 6. The air under positive pressure sweeps the odorants from the blend of odorants into conduit 4 and pushes the odorants through cannula 2 into the nose of the user.

In one aspect, the apparatus is portable to permit treatment over a day/evening. In this aspect, the pump is operated with DC current being supplied by a rechargeable battery. The apparatus has a housing to accommodate the battery and an outlet to effect recharging.

In one form, a CPAP type of machine and/or APAP type of machine can be used to intranasally transmit odorants in a pulsed manner to the olfactory regions of the brain and therefore have a positive effect on the effectiveness of the treatment. In fact, such a use can cut treatment time compared to a CPAP machine continuously intranasally delivering the odorants.

EXAMPLES

To determine if exposure to a blend of multiple odorants will have greater positive impact on olfactory function compared to each odorant alone, 15 adults (40-65 years old; 60% males) with stable moderate olfactory loss were exposed to daily 30-minute long inhalation of limonene (a simple molecule), Rosemary, Lavender or a blend of Rosemary and Lavender. Odor threshold (i.e. minimum concentration of n-butanol detected; higher scores indicate ability to detect higher number of dilutions), odor identification (i.e. the maximum number of odorants identified in a forced-choice test), and odor memory were assessed. In Table 1 below, daily exposure to Lavender or Rosemary significantly improved all 3 olfactory parameters, whereas Limonene did not have any appreciable impact. Those exposed to the blend of Rosemary and Lavender experienced the strongest improvement.

TABLE 1

Effects of Odorant Treatments on Olfaction in 15 Volunteers with Mild Impairments

| Odorant | | #1 | #2 | #3 | #4 | #5 | #6 | #7 | #8 | #9 | #10 | #11 | #12 | #13 | #14 | #15 |
|---|---|---|---|---|---|---|---|---|---|---|---|---|---|---|---|---|
| None | Thresh | 6 | 3 | 5.5 | 3.5 | 1.5 | 2.5 | 3 | 3.5 | 6.5 | 3 | 6 | 3 | 5.5 | 2.5 | 3.5 |
| | Ident | 1 | 5 | 5 | 5 | 5 | 2 | 3 | 2 | 5 | 6 | 7 | 5 | 6 | 3 | 9 |
| | Memory | 4 | 10 | 4 | 14 | 11 | 6 | 11 | 9 | 13 | 9 | 10 | 11 | 9 | 9 | 14 |
| Limonene | Thresh | 2.5 | 5.5 | 5.5 | 3 | 2.5 | 5 | 5.5 | 1.5 | 5.5 | 3 | 6.5 | 5 | 5.5 | 3.5 | 7 |
| | Ident | 2 | 5 | 6 | 4 | 7 | 3 | 3 | 4 | 9 | 5 | 6 | 3 | 9 | 5 | 10 |
| | Memory | 4 | 11 | 5 | 10 | 13 | 10 | 9 | 10 | 14 | 9 | 12 | 10 | 13 | 11 | 12 |
| Lavender | Thresh | 7 | 6.5 | 6 | 3.5 | 5 | | | | | | | | | | |
| | Ident | 9 | 8 | 10 | 6 | 8 | | | | | | | | | | |
| | Memory | 7 | 14 | 11 | 12 | 17 | | | | | | | | | | |
| Rosemary | Thresh | | | | | | 6.5 | 5.5 | 5 | 7.5 | 8 | | | | | |
| | Ident | | | | | | 6 | 10 | 5 | 7 | 9 | | | | | |
| | Memory | | | | | | 10 | 18 | 12 | 16 | 15 | | | | | |
| Combo | Thresh | | | | | | | | | | | 9.5 | 6.5 | 8 | 6.5 | 10.5 |
| | Ident | | | | | | | | | | | 10 | 4 | 8 | 20 | 9 |
| | Memory | | | | | | | | | | | 20 | 18 | 17 | 15 | 19 |

Figure 2A:
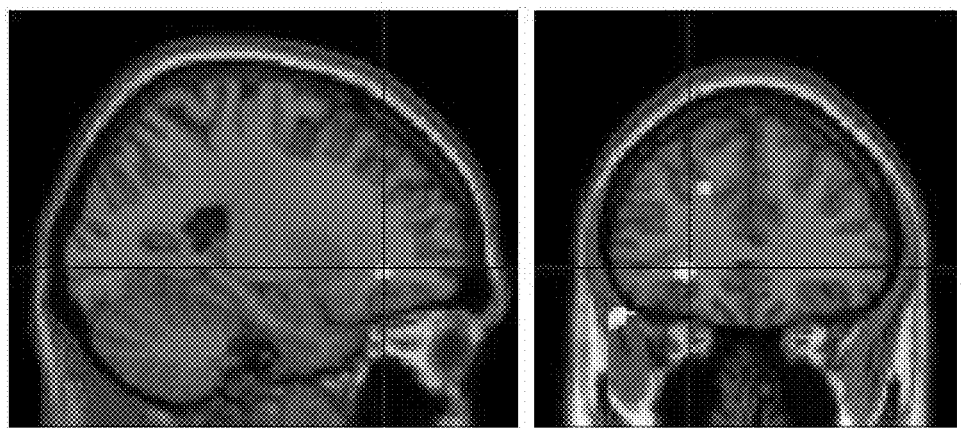
FIG. 2A is an fMRI illustrating activation of olfactory regions.

To explore the impact of daily treatment with OTDS on olfaction, 14 volunteers (70% females; mean age 56.8 years) with combined impairment of odor threshold and odor identification were subjected to one-hourly for 10 days and compared their odor identification and odor threshold pre- and post-treatment. The mean score for the 40-point University of Pennsylvania Smell Identification Task (35), pre- and post-treatment were 30.4 and 36.5, respectively, and this difference was statistically significant. Although the odor threshold also improved with treatment, the change was not statistically significant with 10 days OTDS Additionally, the immediate neural effect of 5 minutes of OTDS treatment on activation of the olfactory region of interest (ROI) using functional magnetic resonance imaging (fMRI). As shown in the representative result (FIG. 2A), orbitofrontal cortex (OFC)—a high-order olfactory processing region—was activated.

Figure 2B:
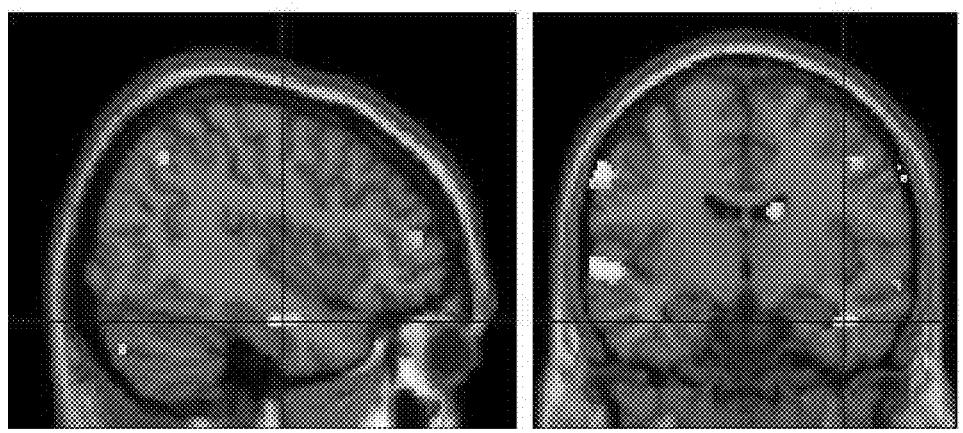
FIG. 2B is an fMRI illustrating activation of additional olfactory regions.

The temporal sequence of short duration (10-sec and 30-sec) repeated olfactory stimulation with the same odorant in the OTDS was tested. As depicted in FIG. 2B, it was observed that activations of more primary olfactory ROI with shorter duration of repeated chemosensory stimulation. In view of this, tests were focused on development of a pulse-based stimulation using the parameters for repeated stimulations and inter-stimulation intervals observed from the fMRI studies.

An OTDS device was reprogrammed for neuromodulation with rOCS. In one form, the device includes User Input/Use Specifications: 1) Input duration of bursts 5-120 seconds with intermittent bursts of no odorant; 10 second interval options; 2) Input frequency of bursts/min; 3) Input amount per burst 0.5-2 ml/min; 3) Should be able to deliver for up to a 1 hour therapy session; 4) History of past uses (7 days); 5) On/Off/In Use light; and 6) Indicator when low on charge/battery and low on fluids (water/odorant). In one form, the device can be portable and have a user-friendly LCD screen menu options (FIG. 3, under Aim 1), that enable configuration of treatment parameters.

Figure 3:
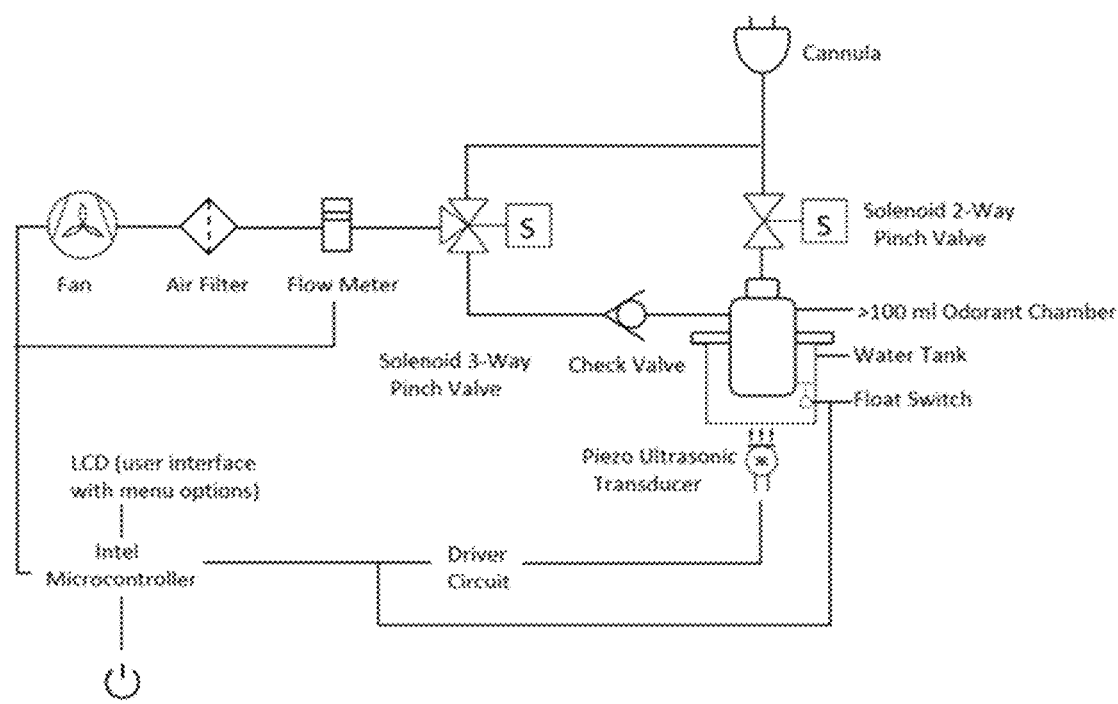
FIG. 3 is an illustration of another form of a device for administration of at least one active ingredient.
Figure 4:
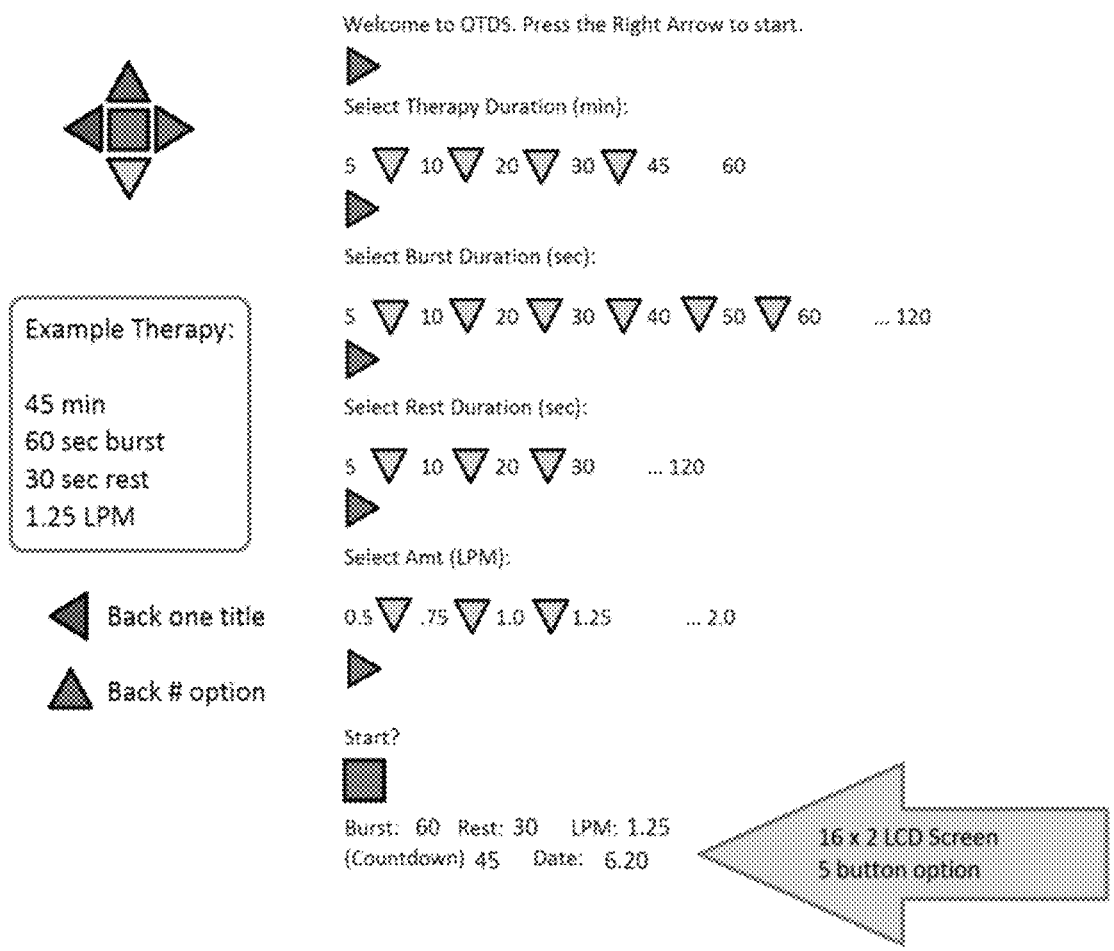
FIG. 4 is depiction of one form of user selectable configuration settings for a device for administration of at least one active ingredient.

In one form, the OTDS is configured as a micro-controller regulated device to deliver repeated bursts or pulses of odorant stimulations with very flexible ranges of pulse parameters to enable targeting of olfactory brain regions impaired during aging. An example of such a device is shown in FIG. 3. Any number of different settings can be configured by medical personnel and/or a user. Examples of other configurable settings are shown in FIG. 4. For example, regulation of: durations of stimulation bursts and inter-burst intervals, burst frequency, input amount of odorants per bursts in liters/minute, and the total duration of treatment may be permitted.

In one form, the device can deliver one or more odorants in discrete bursts where no odor reaches the nose during the rest period.

In one form, the device includes a TDK ultrasonic nebulizer, Arduino UNO R3—Arduino Mega 2560, Adafruit V2 motor shield, solenoid pinch valves, and blower motor.

Figure 5:
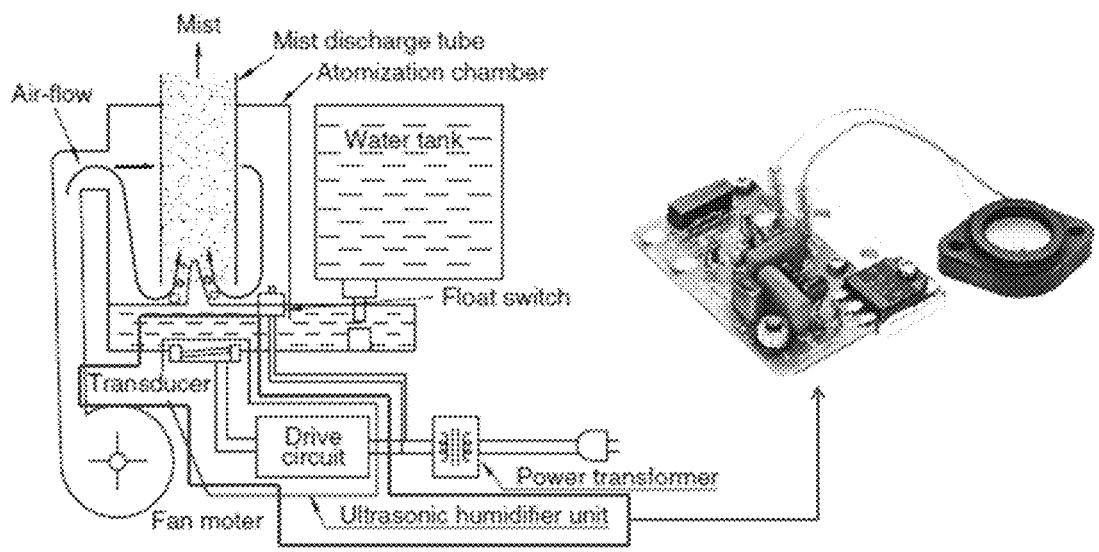
FIG. 5 an illustration of another form of a device for administration of at least one active ingredient.

The ultrasonic nebulizer method (FIG. 5) works by periodic, high frequency vibrations of a piezo-transducer create small bubbles—negative pressure relating to bubble formation, positive pressure creating bubble collapse. The surface of the fluid experiences oscillations making standing capillary waves where water droplets are propelled when they deviate from the sine-like wave shape. Efficiency and droplet size dependent on: ventilation (air pump/fan) psi and Piezo vibration frequency.

As discussed above, the active ingredients, active delivery periods, rest periods, treatment regimens, pressures, concentrations and the like may be modified to stimulate different portions of a user. For example, in one form, three primary olfactory (POC) regions of interest (amygdala, piriform cortex and entorhinal cortex) and the hippocampus may be stimulated in different manners. For example, different portions may react differently to the duration of the active delivery periods and rest periods. For example, very short active delivery periods may stimulate a first portion more than other portions while a longer duration active delivery period may stimulate other portions of a user more than the very short periods. Further, the number of cycles (the number of active delivery periods followed by rest periods) may also impact different portions of a user in different manners.

In one form, the hardware and/or software of the OTDS device for pulsatile delivery of our odorant formulations can be modified as needed for a particular user, odorant, drug, and the like. Similarly, the pulse delivery parameters required to maximally engage the POC can be modified. Further, single odorants, blends of odorants, rotations of single and blends of odorants can be used for engagement of POC and on enduring neuroplasticity. Drugs and other materials may be uses in a similar manner. Further, the device may be portable for home-use.

According to one form, using pulsing, treatment times of 30 minutes are the equivalent of 12 hours with the same odorants where continuous delivery of the odorants is performed.

Pulsing also may be effective for using odorants in the treatment of post-traumatic stress disorder (PTSD), autism, depression and schizophrenia. For example, with PTSD, it is believed that the orbital cortex is not as active and this portion may be made more active by using pulsed treatments. Symptoms of PTSD may be treated by using active delivery periods of about 60 seconds to help activate the orbital cortex. With autism, some symptoms may include lack of development at the amygdala. Shorter active delivery periods, such as about less than 10 seconds, may be used to treat these symptoms. Further, by pulsing, the olfactory bulb may increase in size, resulting from regeneration of neurons.

In one form, a pulsatile approach may deliver odorants for 10 seconds, alternating with 30 seconds break. Therefore, one cycle of treatment is 40 seconds. This gives 45 cycles of treatment over 30 minutes.

A previous approach was a continuous treatment in which some of the key primary olfactory neural elements are inactivated (i.e., turned off) ranging from 45 minutes to 3 hours. Based on a very rough estimation, it requires 24-72 hours to deliver equivalent of 45 cycles of treatment, which is 30 minutes with the new pulsed approach.

While the compositions, uses and forms of apparatus have been particularly described with specific reference to particular process and product embodiments, it will be appreciated that various alterations, modifications, and adaptations may be based on the present disclosure, and are intended to be within the spirit and scope of the application.

What is claimed is:

1. A method for stimulating neurogenesis in selected portions of a user's brain, the method comprising:
    intranasal pulsed administering at least one active ingredient selected from the group consisting of at least one odorant, at least one drug, at least one medicament, and combination thereof, the at least one active ingredient dispersed in a media,
    the pulsed administering including pumping the at least one active ingredient as a part of a flow of gas which includes oxygen and the at least one active ingredient during a plurality of active delivery periods which are each followed by a rest period where no active ingredients are delivered, the active delivery periods being between about 1 and about 600 seconds,
    the concentration of the at least one active ingredient, the rate of flow of the blend and oxygen, the duration of the active delivery periods and rest periods, and a time of treatment effective for stimulating neurogenesis in selected portions of a user,
    wherein the at least one active ingredient includes rosemary, wherein the rosemary includes carnosic acid in an amount of at least 3 wt. %.

2. The method of claim 1 wherein the active delivery periods are about 1 to about 10 seconds to stimulate a first portion of the user.

3. The method of claim 1 wherein the active delivery period are about 30 to about 45 seconds to stimulate a second portion of the user.

4. The method of claim 1 wherein the active delivery period are about 60 to about 120 seconds to stimulate a second portion of the user.

5. The method of claim 1 wherein the rest periods are from about 10 to about 120 seconds.

6. The method of claim 1 wherein a plurality of different active ingredients is administered separately over different active delivery periods.

7. A method for stimulating neurogenesis in selected portions of a user's brain, the method comprising:
- intranasal pulsed administering at least one active ingredient selected from the group consisting of at least one odorant, at least one drug, at least one medicament, and combination thereof, the at least one active ingredient dispersed in a media,
- the pulsed administering including pumping the at least one active ingredient as a part of a flow of gas which includes oxygen and the at least one active ingredient during a plurality of active delivery periods which are each followed by a rest period where no active ingredients are delivered, the active delivery periods being between about 1 and about 600 seconds,
- the concentration of the at least one active ingredient, the rate of flow of the blend and oxygen, the duration of the active delivery periods and rest periods, and a time of treatment effective for stimulating neurogenesis in selected portions of a user,
- wherein the at least one active ingredient comprises a blend of at least two odors selected from the group consisting of orange, lemon, rosemary, cinnamon, banana oil, cumin, vanillin, ethylvanillin, garlic, paprika, curry, nutmeg, thyme, tarragon, celery, ginger, lavender, marjoram, basil leaves, cardamom, cloves, chocolate and anise odorants.

8. The method of claim 1 wherein the flow of gas through the nose is from about 0.5 to about 2 liters per minute.

9. The method of claim 1 wherein the at least one active ingredient is in a concentration in the range of from about 0.5 to about 6.0 weight percent.

10. A method for activating selected areas of a user's brain with active ingredients comprising:
- delivering at least one active ingredient by pulsing by positive pressure a flow of the at least one active ingredient dispersed in a gas and controlling the area of the brain being activated by selecting a pulse and rest period that will selectively stimulate the selected area of the brain,
- wherein the at least one active ingredient includes rosemary, wherein the rosemary includes carnosic acid in an amount of at least 3 wt. %.

* * * * *